United States Patent
Rubio Nistal et al.

(10) Patent No.: US 10,179,153 B2
(45) Date of Patent: Jan. 15, 2019

(54) PROBIOTIC AND PREBIOTIC COMPOSITIONS

(71) Applicants: AQUILON CYL SOCIEDAD LIMITADA, León (ES); UNIVERSIDAD DE LEÓN, León (ES)

(72) Inventors: Pedro Miguel Rubio Nistal, Leon (ES); Ana Maria Carvajal Urueña, Leon (ES); Marta García Díez, Leon (ES)

(73) Assignees: Universidad De Leon, Leon (ES); Aquilon CYL S.L., Leon (ES)

( * ) Notice: Subject to any disclaimer, the term of this patent is extended or adjusted under 35 U.S.C. 154(b) by 0 days.

(21) Appl. No.: 15/520,622

(22) PCT Filed: Oct. 21, 2015

(86) PCT No.: PCT/EP2015/074375
§ 371 (c)(1),
(2) Date: Apr. 20, 2017

(87) PCT Pub. No.: WO2016/062771
PCT Pub. Date: Apr. 28, 2016

(65) Prior Publication Data
US 2017/0312321 A1   Nov. 2, 2017

(30) Foreign Application Priority Data

Oct. 21, 2014   (EP) ..................... 14382412

(51) Int. Cl.
*A01N 63/00* (2006.01)
*A61K 35/747* (2015.01)
*A61K 35/74* (2015.01)
*A61K 35/744* (2015.01)
*C12R 1/25* (2006.01)
*C12R 1/225* (2006.01)
*C12N 1/20* (2006.01)

(52) U.S. Cl.
CPC ............ *A61K 35/747* (2013.01); *A61K 35/74* (2013.01); *A61K 35/744* (2013.01); *C12N 1/20* (2013.01); *C12R 1/225* (2013.01); *C12R 1/25* (2013.01); *Y02A 50/473* (2018.01); *Y02A 50/481* (2018.01)

(58) Field of Classification Search
CPC .................................................. A61K 35/747
See application file for complete search history.

(56) References Cited

U.S. PATENT DOCUMENTS

2007/0116671 A1* 5/2007 Prakash ............... A61K 9/0024
424/93.2
2014/0023620 A1   1/2014 Ioudina

FOREIGN PATENT DOCUMENTS

| EP | 1034788 A1 | 9/2000 |
| EP | 1997499 A1 | 12/2008 |
| WO | WO-2005007834 A1 | 1/2005 |
| WO | WO-2014049023 A1 | 4/2014 |

OTHER PUBLICATIONS

Kim, H.I. et al., "Acid tolerant probiotic Enterococcus faecalis probio-056 that can suppress the growth of pathogenic microorganisms and PED (porcine epidemic diarrhea) coronavirus" WPI/Thomson, 1 page. Mar. 10, 2005, XP002428799, Abstract.
Seo, B.I. et al., "Bile tolerant *Lactobacillus reuteri* isolated from pig feces inhibits enteric bacterial pathogens and porcine rotavirus", *Veterinary Research Communications* (2010) vol. 34, pp. 323-333.

* cited by examiner

*Primary Examiner* — Albert M Navarro
(74) *Attorney, Agent, or Firm* — McCarter & English, LLP; Jill Ann Mello

(57) ABSTRACT

The invention relates to products and compositions that may be beneficial in animal husbandry. Said products and compositions comprise microorganisms, such as bacteria, and probiotic bacteria in particular. Thus, provided herein are microbial strains, as well as selection criteria which will enable the skilled reader to find further strains useful in the present invention. The strains, as well as compositions comprising the same, may be administered to animals, farmed animals such as swine in particular. The administration may occur in the first days of life. By administration of the products or compositions of the inventions animal growth can be promoted and animal weight can be increased. Infections may also be prevented or treated by said compounds or compositions.

12 Claims, 2 Drawing Sheets

PROBIOTIC AND PREBIOTIC COMPOSITIONS

RELATED APPLICATIONS

This application is a 35 U.S.C. § 371 national stage filing of International Application No. PCT/EP2015/074375, filed Oct. 21, 2015, which claims priority to European Patent Application No. 14382412.6, filed Oct. 21, 2014. The entire contents of each of the foregoing applications are incorporated herein by reference.

TECHNICAL FIELD

The present invention relates to the field of biotechnology, particularly to probiotics and to compositions comprising probiotics which may be useful in the treatment of humans and/or animals.

BACKGROUND ART

Newborn animals and those in (intense) farming in particular, are prone to bacterial and other infections such as viral infections. These infections can lead to diarrhoea associated with weight loss and, in severe cases, even to death of the newborn. For example, several years ago, diarrhoeal cases in newborn piglets have been described in swine farms from different geographical situations in Spain. It is believed that said diarrhoea is a symptom in these animals, whereas the causative factor of said symptom is sometimes difficult to locate. In many cases of diarrhoea in newborn swine for example, it is possible to isolate possibly unfavorable/undesired bacterial strains, such as *Escherichia coli*, alone or in combination with *Clostridium perfringens* or *Clostridium difficile*, but diarrhoea is usually detected just after birth and routine treatment and prophylaxis procedures are oftentimes not effective. In other cases, diarrhoea is caused, for example, by viral infections, such as infections caused by rotavirus, coronavirus, norovirus adenovirus and/or astrovirus.

Without wishing to be bound to any particular theory, it is believed that dysbiosis (also called dysbacteriosis) may be a causative factor. Dysbiosis refers to a condition with microbial imbalances on or within the body. In farming animals, swine in particular, dysbiosis may be caused by indiscriminate use of antibiotics during sow maintenance, producing alterations in newborn piglet's intestinal flora.

In view of these disadvantages of the use of antibiotics, it is recommended to reduce the use of antibiotics in animal husbandry. On the other hand, alternative methods of treatment of the newborn animals would then be required to replace the commonly used antibiotics.

Since the EU recommends since 2005 to reduce the use of antibiotics as growth promoters in swine breading (Amended by Regulation (EC) No 378/2005 of 4 Mar. 2005), animal breeders are longing for alternatives which can improve the general health status of (farm) animals, particularly in the early days of life. The present inventors provide a solution to this problem, and said solution is described in the following. The present invention thus solves several problems caused by state of the art methods, and the advantageous effects will be detailed below.

BRIEF DESCRIPTION OF THE INVENTION

In a first aspect, the invention relates to a composition comprising at least the strain deposited at Spanish Type Cultures Collection with deposit number CECT 8700 (AqSynRMH69).

In addition, the invention relates to a composition comprising a mixture of microorganisms, wherein the microorganisms belong to the species *Lactobacillus plantarum* and *Lactobacillus reuteri*, and optionally including at least one microorganism belonging to the genera *Lactobacillus* (preferably with the exception of microorganisms belonging to the species *Lactobacillus fermentum* and *Lactobacillus mucosae*, preferably these microorganisms being CECT 8347 (AqSynJ12) and CECT 8349 (AqSynJ55), respectively) *Leuconostoc*, *Pediococcus*, *Lactococcus*, *Streptococcus Aerococcus*, *Carnobacterium*, *Enterococcus*, *Oenococcus*, *Sporolactobacillus*, *Tetragenococcus*, *Vagococcus* and/or *Weisella*, for use in a method for treating a human or animal.

*Lactobacillus fermentum* CECT 8347 (AqSynJ12) and *Lactobacillus mucosae* CECT 8349 (AqSynJ55) were deposited by Aquilón CYL S.L. with the CECT (Spanish Type Cultures Collection, Colección Española de Cultivos Tipo (CECT), Universidad de Valencia, Parc Cientific Universitat de València, Catedrático Agustín Escardino, 9, 46980 Paterna (Valencia, Spain)) on May 16, 2013.

In a preferred embodiment, the composition of the invention comprises two lactic acid bacterium which are CECT 8700 (AqSynRMH69) and CECT 8350 (AqSynJ59), which were deposited in the CECT (Colección Española de Cultivos Tipo (CECT), Universidad de Valencia, Parc Cientific Universitat de València, Catedrático Agustín Escardino, 9, 46980 Paterna (Valencia, Spain)) by Aquilón CYL S.L.

In one embodiment, in the composition of the invention, each strain fulfils at least the following condition a., and preferably both conditions a. and b., and most preferably all conditions a., b. and c.:

a. shows an antimicrobial activity evidenced by at least one of the following inhibition zones: (i) 10 mm or more, for example 13 mm or more, for *Salmonella*, (ii) 9 mm or more, preferably 10 mm or more, for *Listeria monocytogenes*, (iii) 9 mm or more, preferably 10 mm or more, for *Staphyloccocus aureus*, (iv) 10 mm or more, for example 18 mm or more, for *Escherichia coli*;

b. is able to retain essentially the same viability during 3 hours of incubation at pH=3.5, or, alternatively at pH=2.5;

c. is able to retain essentially the same viability during 4 hours of incubation in presence of 0.45% bile extract, preferably at pH=8.

"Viable organisms" may be defined as organisms and any life stages thereof that are living. Accordingly, a strain which is "able to retain essentially the same viability" may mean a strain which is able to survive and keep alive under certain conditions, for example that 50% or more CFU, such as 50%, or 60%, or 70%, or 75%, or 80%, or 95%, 99% or more, such as 100% CFU are alive (viable) after being exposed to certain conditions (e.g., 3 hours of incubation at pH=3.5, or, alternatively at pH=2.5, and/or 4 hours of incubation in presence of 0.45% bile extract, preferably at pH=8).

The composition of the invention in any of its variants may be for use in a method for treating a human or an animal, such as for example in a method for treating or preventing diarrhoea. In this case, the diarrhoea may be caused by a bacterial infection. In addition, the diarrhoea may be caused by a viral infection. Moreover or alternatively, the composition of the invention in any of its variants, for use in a method for treating a human or an animal may be used for increasing weight of a newborn mammal (preferably a piglet). The composition may be administered to the mammal, preferably to a newborn mammal, preferably to a newborn animal and more preferably to a piglet.

The invention also provides a microorganism, preferably a bacterium, and more preferably a lactic acid bacterium. The microorganism provided by the invention is the strain CECT 8700 (AqSynRMH69), which was deposited with CECT (Spanish. Type Cultures Collection, Colección Española de Cultivos Tipo (CECT), Universidad de Valencia, Pare Cientific Universitat de Valéncia, Catedrático Agustín Escardino, 9, 46980 Paterna (Valencia, Spain)) by AQUILON CYL S.L. on Sep. 10, 2014.

AqSyn numbers in brackets, which can be used synonymously for each of the strains, were allocated to the strains by the present inventors.

Preferably the composition of the invention comprises the strain CECT 8700 (AqSynRMH69) and at least one further strain. Preferably, the at least one further strain is selected from strains belonging to the genera *Lactobacillus* (preferably with the exception of microorganisms belonging to the species *Lactobacillus fermentum* and *Lactobacillus mucosae*, preferably these microorganisms being CECT 8347 (AqSynJ12) and CECT 8349 (AqSynJ55), respectively), *Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*.

In a preferred embodiment, the composition comprises or, alternatively, consists of at least the following strains: CECT 8700 (AqSynRMH69) and CECT 8350 (AqSynJ59). Optionally, the composition may comprise further strains. Preferably, the composition does not comprise any further strain. Accordingly, the preferred composition comprises microorganisms which consists of CECT 8700 (AqSynRMH69) and CECT 8350 (AqSynJ59) (namely the composition comprises the following microorganisms CECT 8700 (AqSynRMH69) and CECT 8350 (AqSynJ59) and it may comprise further components which are not microorganisms).

Preferably, the microorganisms comprised in the composition of the invention are antibiotic resistant, as described in more detail below.

In either case "comprises" may optionally be understood in that further bacterial strains are present, or that no further bacterial strains are present. Even if no further bacterial strains are present, "comprises" may optionally mean that further other ingredients, i.e. any ingredients other than bacteria are present.

The strain CECT 8350 (AqSynJ59) was deposited with CECT (Spanish Type Cultures Collection, Colección Española de Cultivos Tipo (CECT), Universidad de Valencia, Parc Cientific Universitat de València, Catedrático Agustín Escardino, 9, 46980 Paterna (Valencia, Spain)) by AQUILON CYL S.L on May 16, 2013.

The terms "treatment" or "therapy" encompass both prophylactic and curative methods of treating disease, since both are directed to the maintenance or restoration of health. Irrespective of the origin of pain, discomfort or incapacity, its relief, by the administration of an appropriate agent, is to be construed as therapy or therapeutic use in the context of the present application.

In some embodiments the composition of the invention (in any embodiment described) may be used for example in a method for treating a human or an animal, such as for example in a method for treating or preventing diarrhoea and/or for increasing weight of a newborn mammal and/or in a method for promoting growth of a newborn mammal. Preferably, the composition may be used in a method for treating an animal, such as for example in a method for treating or preventing diarrhoea and/or for increasing weight of a newborn mammal and/or in a method for promoting growth of a newborn mammal, such as a newborn piglet. The diarrhoea may be caused by bacteria and/or by viral infection (namely, a bacterial infection and/or a viral infection may be the cause of the diarrhoea in the newborn mammal).

The composition of the invention is particularly suitable for treating or preventing a condition in a mammal, as described above, such as diarrhoea and/or an infection, such as a bacterial infection and/or a viral infection. In some embodiments the condition may be selected from diarrhoea due to bacterial infections (including collibacilosis), *Clostridium difficile* newborn diarrhoea, *Clostridium perfringens* A and C type. In some embodiments the condition may be selected from diarrhoea due to viral infections, such as rotavirus infections, coronavirus infections, norovirus infection, adenovirus infections and/or astrovirus infections, preferably rotavirus infections and/or coronavirus infections. It is also possible to administer the composition to animals suffering from diarrhoea, even if a (bacterial and/or viral) infection has not (yet) been proven to be the causative factor for said diarrhoea. The composition of the invention may also be administered before the animal has any diarrhoea and/or infection, in order to prevent the diarrhoea and/or infection.

DETAILED DISCLOSURE OF THE INVENTION

Figure 1:
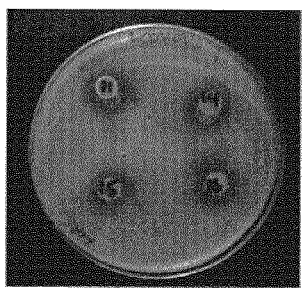
FIG. 1: Inhibition zones, illustrative example.

The following detailed description discloses specific and/or preferred variants of the individual features of the invention. The present invention also contemplates as particularly preferred embodiments those embodiments which are generated by combining two or more of the specific and/or preferred variants described for two or more of the features of the present invention.

Unless expressly specified otherwise, the term "comprising" is used in the context of the present document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

Unless expressly specified otherwise, all indications of relative amounts in the present application are made on a weight/weight basis. Indications of relative amounts of a component characterized by a generic term are meant to refer to the total amount of all specific variants or members covered by said generic term. If a certain component defined by a genetic term is specified to be present in a certain relative amount, and if this component is further characterized to be a specific variant or member covered by the generic term, it is meant that no other variants or members covered by the generic term are additionally present such that the total relative amount of components covered by the generic term exceeds the specified relative amount; more preferably no other variants or members covered by the generic term are present at all.

As used herein, the term "about" means the indicated value±1% of its value, or the term "about" means the indicated value±2% of its value, or the term "about" means the indicated value±5% of its value, the term "about" means the indicated value±10% of its value, or the term "about" means the indicated value±20% of its value, or the term "about" means the indicated value±30% of its value; preferably the term "about" means exactly the indicated value (±0%).

The present invention integrates the concept of probiotics and prebiotics, thereby providing synbiotics. The inventors open a new therapeutic window of bacteria and compositions having an immune modulator effect. The microorganisms or compositions of the invention may be administered at an early life stage of an animal, such as a piglet. Thus, the invention relates to products and compositions that may be beneficial in animal husbandry. The real important observation, as evidenced by the examples, is that the probiotic treatment is at least equally effective, and most probably better (compared to standard antibiotic treatment), in terms of productivity to the treatment with antibiotics. The inventors' contribution has a huge economic impact both because of the overall cost of treatment and because of legal pressure and environmental impact.

The microorganisms, preferably bacteria that can be used according to the invention are microorganisms with beneficial effects. They are preferably lactic acid bacteria. Even non-bacterial species of microorganisms can be used according to the present invention, as long as they comply with the selection criteria a. to c. below. For example, it is known that some yeast can have probiotic properties too.

Although the functional parameters described herein are the most important selection criteria, as far as species of the microorganisms are concerned, lactic acid bacteria are preferred. Lactic acid bacteria (LAB) comprise a Glade of Grain-positive, acid-tolerant bacteria that are associated by their common metabolic and physiological characteristics. These bacteria, naturally found in decomposing plants and lactic products, as well as in animal feces, produce lactic acid as a major metabolic end-product of carbohydrate fermentation. Lactic acid bacteria are generally reco sized as safe (GRAS status), due to their ubiquitous appearance in food and their contribution to the healthy microflora of mammalian mucosal surfaces. Lactic acid bacteria are preferably selected among the genera *Lactobacillus, Leuconostoc, Pediococcus, Lactococcus, Streptococcus Aerococcus, Carnobacterium, Enterococcus, Oenococcus, Sporolactobacillus, Tetragenococcus, Vagococcus*, and *Weisella*. *Lactobacillus* and/or *Enterococcus* may be preferred. *Lactobacillus* is preferred. In an embodiment of the present invention, microorganisms belonging to the species *Lactobacillus fermentum* and *Lactobacillus mucosae* may not be present in the composition of the present invention. Particularly, in an embodiment of the present invention, microorganisms belonging to *Lactobacillus fermentum* CECT 8347 (AqSynJ12) and *Lactobacillus mucosae* CECT 8349 (AqSynJ55) may not be present in the composition of the present invention.

The bacteria preferred herein are preferably Gram positive and are catalase negative. Whether a bacterium is Gram positive can be tested according to standard technologies known in the art. Gram staining consists in consecutive staining with different "colorings" (stains) and washing of the sample in order to check if it is positive or negative. Whether a bacterium is catalase negative is tested as follows: The catalase test involves adding hydrogen peroxide to a culture sample or agar slant. If the bacteria in question produce catalase, they will convert the hydrogen peroxide and oxygen gas will be evolved. The evolution of gas causes bubbles to form and these bubbles are indicative of a positive test (catalase positive bacterium).

The lactic acid bacteria preferred herein are preferably able to grow in MRS (Man Rogosa Sharpe) medium, and more preferably in acidified MRS agar as described below. MRS medium was created for favouring the growth of lactic acid bacteria, especially *Lactobacillus* sp. It is believed to disfavour the growth of the vast majority of Gram negative bacteria. However, other bacteria than lactic acid bacteria may eventually grow in MRS, and it is therefore recommendable or even necessary to check that the colonies belong to Gram positive and are catalase negative bacteria.

The lactic acid bacteria preferred herein may possibly be probiotic bacteria. The most commonly accepted definition of "probiotic" was given in 1998 by Füller, who described it as "a live microbial feed supplement which beneficially affects the host animal by improving its intestinal microbial balance". Generally, probiotics are live microorganisms. It is believed that different probiotics have different actions in the gut, and different probiotics may therefore act together to provide a beneficial effect. Other sources define probiotics as those microorganisms for which a health benefit on the human or animal has already been proven. Selection criteria for probiotics are published in: "Report of a Joint FAO/WHO Expert Consultation on Evaluation of Health and Nutritional Properties of Probiotics in Food Including Powder Milk with Live Lactic Acid Bacteria", Food and Agriculture Organization of the United Nations and World Health Organization, 2001, Cordoba, Argentina. The advantages of the use of life bacteria have been widely described.

In recent years, the concept of "prebiotics" was introduced; prebiotics are non-digestible food components that increase the growth of specific microorganisms in the gastrointestinal tract. "Synbiotics" are compositions comprising at least one probiotic and at least one prebiotic. Such compositions are understood to encourage the growth of beneficial bacteria (e.g. the probiotics). As an illustrative example, fermented dairy products are oftentimes considered as synbiotics because they contain live bacteria and the food source needed for them. Although benefits associated with prebiotics and probiotics are favorable, researchers are cautious about drawing general conclusions because benefits vary, depending on type and amount of pre- and probiotic consumed, as well as specific combinations of specific probiotics with specific prebiotics. Thus, powerful synbiotics are based on a combination of specific strains of probiotic bacteria with carefully selected prebiotics. They can lead to an important health benefit to a mammal.

Specific probiotics, prebiotics and synbiotics have been suggested for uses in humans and selection criteria for probiotics are disclosed for example in "Report of a Joint FAO/WHO Expert Consultation on Evaluation of Health and Nutritional Properties of Probiotics in Food Including Powder Milk with Live Lactic Acid Bacteria", Food and Agriculture Organization of the United Nations and World Health Organization, 2001, Cordoba, Argentina.

The present invention uses microorganisms, bacteria in particular, which have a potential of showing a health benefit on animals, farm animals in particular. Preferably, the animal is a domestic, domesticated animal or an animal which itself is not domestic or domesticated (i.e. wild) but which belongs to the same species or genus as a domestic animal. A wild pig for example would be included in this definition since it belongs to the same species as a domestic pig. Some examples of domestic animals that can be treated include without limitation dogs, cats and other pets, horses, cattle, chicken and other poultry, swine, sheep, goats. Preferably the animal is a farm animal, and farm animals include without limitation horses, cattle, chicken and other poultry, swine, sheep, goats. More preferably, the animal is from the suborder Suina. The suborder Suina (also known as Suifomies) is a lineage of mammals that includes the pigs and peccaries of the families Suidae and Tayassuidae. Swine or pig, either wild or domestic, may be particularly preferred.

The strains which are suitable for the present invention (namely that may be comprised in the composition of the present invention) can be identified as follows.

First Step for Arriving at the Strains of the Invention: Isolation of Single Strains In a first step, a sample containing microorganisms (preferably bacteria) is isolated. Any source of microorganisms can be suitable, which in the broadest sense can be any non-sterile sample from nature. The source may be from (domestic) animals, such as from young animals in the first 30 days of life, or from their mothers. Alternatively, the source may be from wild animals (e.g. wild boars), such as samples collected from captured wild boars. Suitable sources include colostrum from mother animals (e.g. sows), meconium samples from newborn animals (e.g. piglets), intestinal wall washes from domestic or wild animals or natural intestinal lactic acid bacteria. Microorganisms (e.g. bacteria) contained in the samples may be grown on growth media well known in the art to be suitable for growth of intestinal microorganism, e.g. MRS medium. The microorganisms may be streaked out, which will enable the isolation of single colonies. The single colonies can be picked and the respective strains further propagated in a suitable growth medium (for example the same as was used initially).

The strains of these single colonies are optionally tested by Gram staining by methods known in the art (and selected if they are Gram positive) and/or tested for the presence of Catalase activity as described above (and selected if they are Catalase negative).

Second Step of Arriving at the Strains of the Invention: In Vitro Tests

In order to be selected as useful for the present invention, a microorganism strain, originating preferably from the first step described above, must fulfil at least one of the following criteria which are first listed here and then detailed below:

a. Activity against undesired bacteria;
b. Acid tolerance;
c. Bile salts tolerance;

The items a. to c. represent priority; i.e. it is most desired that criterion a. is met, second-most-desired that criteria a. and b. are met, and most preferred that all criteria a. to c. are met. The selection criteria are detailed as follows.

a. Activity Against Undesired Bacteria

In vitro screening against undesired bacteria is done. "Undesired" are bacteria selected from the following one or more: *Salmonella* sp., *Listeria monocytogenes, Staphyloccocus aureus* and *Escherichia coli*. Preferably, the *Salmonella* species is *Salmonella enterica*, more preferably *Salmonella enterica* serotype *Typhimurium*.

The activity against the undesired bacteria is tested according to the spot on lawn test, which is described in the following. Liquid overnight cultures (MRS) of each strain to be tested are applied as single spots of 10 µl on MRS agar and incubated at 30° C. for 24 h in anaerobic conditions. After incubation, the plates are covered with 7 ml of semi-solid BHI agar (0.7%) inoculated with one of the undesired bacteria (1%; 1 ml overnight culture in 100 ml medium). Separate plates containing one particular strain to be tested are overlaid with one of the undesired bacteria species, respectively. Each such test is performed in triplicate. After incubation for 24 h at or near the optimal growth temperature of the undesired bacterium (which optimal growth temperature is known in the art for each of the undesired bacteria referred to herein), the samples are examined for evidence of inhibition. To that end it is first checked if an inhibition zone is present. If so, the diameter of the inhibition zone is measured optically. In events where the inhibition zone appears not exactly circular the measurement of the inhibition zone is done with a rule of measuring the inhibition zone's shortest diameter. Finally, the arithmetic mean of the triplicate experiment is determined and it is checked if the following criterium is met.

CRITERIUM: At Least One of the Following Conditions [(i), (ii), (iii), (iv)] Must be Fulfilled for a Strain in Order to be Selected as Positive:

For *Salmonella*, inhibition zone 10 mm or more, for example 13 mm or more.

For *Listeria monocytogenes*, inhibition zone 9 mm or more, for example 10 mm or more.

(iii) For *Staphyloccocus aureus*, inhibition zone 9 mm or more, for example 10 mm or more.

(iv) For *Escherichia coli*, inhibition zone 10 mm or more, for example 18 mm or more.

9 mm or more includes 10 ram or more, 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 31 mm or more, 32 mm or more, 33 mm or more, 34 mm or more, 35 mm or more.

10 mm or more includes 11 mm or more, 12 mm or more, 13 mm or more, 14 mm or more, 15 mm or more, 16 ram or more, 17 mm or more, 18 ram or more, 19 mm or more, 20 mm or more, 21 mm or more, 22 mm or more, 23 mm or more, 24 mm or more, 25 mm or more 26 mm or more, 27 mm or more, 28 mm or more, 29 mm or more, 30 mm or more, 35 mm or more.

13 mm or more includes 14 mm or more, 15 mm or more, 16 mm or more, 17 mm or more, 18 mm or more, 19 mm or more, 20 mm or more, 19 mm or more, 20 mm or more, 25 mm or more, 30 mm or more.

18 mm or more includes 19 or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more.

A composition comprising several strains can also be tested for the above criteria, and such composition, in order to be selected to be suitable for any of the uses described herein, must fulfil at least one, and more preferably all of the criteria [(i), (ii), (iii), (iv)]. It can also be expected that such a composition can suitably be prepared by combining individual microorganism strains of which everyone fulfils at least one of the criteria (i), (ii), (iii), (iv); but whether this is really the case must be experimentally tested.

Alternatively, the agar well diffusion assay may be used for determining inhibition zones. This process eliminates any traces of lactic acid that could be produced in low glucose MRS broth by neutralizing cell-free supernatants. Stationary phase cultures of the species to be tested, grown under anaerobic conditions, are harvested by centrifugation (5000 g/20 min/4° C.), and the pH of the cell-free supernatant is adjusted to 6.5 with 1M NaOH. Supernatants are filter-sterilized (0.20 mm; Millipore Ltd., Hertfordshire, England). The cell-free supernatant (30 µl) is added to 7-mm diameter wells cut into agar plates inoculated with [approximately] $10^5$ colony-forming units (CFU)/ml of the undesired bacterium listed in (i), (ii), (iii), (iv). The agar plates are then incubated at 30° C. for 24 hours. The diameter of the inhibition zones around the wells is measured, and selection criteria are as indicated under (i), (ii), (iii), (iv) above, of which at least one must be fulfilled for a strain to be selected as positive.

For information: the assays above are based on what has been described by Kawai et al., 2004. Applied and Environmental Microbiology 70(5): 2906-2911; Dortu et al. 2008. Letters in Applied Microbiology, 47: 581-586; Hata et al., 2009. International Journal of Food Microbiology, 137: 94-99, Awaisheh 2009. Food Pathogens and Disease 6 (9): 1125-1132.).

b. Acid Tolerance

Acid can be seen as mimicking gastric juice, and tolerance thereto may be tested as follows. 100 µl of an initial suspension in MRS of a 6-8×10$^8$ CFU/ml of each strain are suspended in acidified MRS (pH=3.5, or, alternatively pH=2.5) acidified upon addition of appropriate amount of 12 N HCl) and incubated 37° C. under 110 rpm agitation. Samples are tested by colony count (CFU/ml) at hour 0, 3 and 6. Any other method known to the skilled person to test the acid tolerance may be used.

CRITERIUM: The strain must be able to retain essentially the same viability (at least 50%, or at least 55%, or at least 60%, or at least 70%, or at least 75%, or at least 80%, or at least 95% CFU after the test compared to before, most preferably at least 50% CFU after the test compared to before) during 3 hours of incubation in said medium. For reference: a similar protocol is briefly described by Huang et al., International Journal of Food Microbiology 91: 253-260).

c. Bile Salts Tolerance

Simulation of the mammal's natural small intestine conditions.

The bile salts tolerance may be tested as follows: 100 µl of an initial suspension in MRS of a 6-8×10$^8$ CFU/ml of a bacterial strain are suspended in simulated small intestine solution (e.g. MRS at pH=8 (pH adjusted upon addition of NaOH) and 0.45% bile extract (Bile extract, porcine. B8631-100G. SIGMA-ALDRICH)) and incubated 37° C. under 110 rpm agitation. Samples were tested by colony count (CFU/ml) at hour 1, 2 and 4. Any other method known to the skilled person to test the bile salts tolerance may be used.

CRITERIUM: No loss of viability (or essentially no loss of viability, i.e. preferably 50% or more CFU, such as 50%, or 60%, or 70%, or 75%, or 80%, or 95% or more CFU) after exposure to simulated small intestine juices (0, 45% bile salts, optionally at pH=8) for 4 hours. A similar protocol is briefly described by Huang et al., International. Journal of Food Microbiology 91: 253-260.

Optionally, the strains that had been identified as positive by the above criteria a. to c. can also be tested for their adherence to epithelial surfaces and persistence in the animal (e.g. swine) gastrointestinal tract. It is believed that strains with good adherence properties will perform best.

Optionally, the strains that had been identified as positive by the above criteria a. to c. are additionally tested for their antibiotic resistance profile, e.g. by the Minimal antibiotic concentration test (VetMIC microplate tests) and/or a genotypic resistance test is performed by performing a PCR for different resistance genes (Egervarn et al., 2010. Antonie van Leeuwenhoek 97: 189-200). It is believed that bacteria with no antibiotic resistance (absence or inactivity/loss-of-function of resistance genes) are most suited for application to farm animals.

In a preferred embodiment, at least one strain, and preferably all strains comprised in the composition fulfil all criteria a. to c. as describe above. In addition, with regard to criteria a., the at least one strain, an preferably all the strains comprised in the composition have all of the following antimicrobial activities, as evidenced by inhibition zones determined by the spot on lawn assay: (i) 10 mm or more inhibition zone for *Salmonella*, (ii) 9 mm or more inhibition zone for *Listeria monocytogenes*, (iii) 9 mm or more inhibition zone for *Staphyloccocus aureus*, (iv) 10 mm or more inhibition zone for *Escherichia coli*.

The present invention provides a composition comprising at least the strain deposited at Spanish Type Cultures Collection, Colección Española de Cultivos Tipo (CECT), Universidad de Valencia, Parc Cientific Universitat de València, Catedrático Agustín Escardino, 9, 46980 Paterna (Valencia, Spain)) by AQUILON CYL S.L., with deposit number CECT 8700 (AqSynRMH69) on Sep. 10, 2014. The composition of the invention may further comprise at least one strain of microorganisms, such as at least one, or at least two, or at least three, or at least four, or at least five, or at least six, or at least seven, or at least eight, and so forth, wherein each further strain has at least one of the following antimicrobial activities, as evidenced by inhibition zones determined by the spot on lawn assay: (i) 10 mm or more inhibition zone for *Salmonella*, (ii) 9 mm or more inhibition zone for *Listeria monocytogenes*, (iii) 9 mm or more inhibition zone for *Staphyloccocus aureus*, (iv) 10 mm or more inhibition zone for *Escherichia*

This at least one further strain comprised in the composition may preferably be selected from the strains belonging to the group consisting of the genera *Lactobacillus* (preferably with the exception of *Lactobacillus fermentum* (preferably CECT 8347 (AqSynJ12)) and *Lactobacillus mucosae* (preferably CECT 8349 (AqSynJ55)), *Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*.

For example, the composition comprises or, alternatively, consists of CECT 8700 (AqSynRMH69) and at least one, and preferably one, further strain selected from the group consisting of: CECT 8163 (AqSyn04); CECT 8165 (AqSyn06); CECT 8164 (AqSyn09); CECT 8166 (AqSyn10), CECT 8347 (AqSynJ12); CECT 8348 (AqSynJ17); CECT 8349 (AqSynJ55) and CECT 8350 (AqSynJ59).

CECT 8163 (AqSyn04); CECT 8165 (AqSyn06); CECT 8164 (AqSyn09); CECT 8166 (AqSynJ10), CECT 8347 (AqSynJ12); CECT 8348 (AqSynJ17); CECT 8349 (AqSynJ55) and CECT 8350 (AqSynJ59) were all deposited with CECT (Spanish Type Cultures Collection, Colección Española de Cultivos Tipo (CECT), Universidad de Valencia, Parc Cientific Universitat de València, Catedrático Agustín Escardino, 9, 46980 Paterna (Valencia, Spain)) by AQUILON CYL. S.L. CECT 8163 (AqSyn04); CECT 8165 (AqSyn06); CECT 8164 (AqSyn09) and CECT 8166 (AqSyn10) were deposited on Jun. 20, 2012. CECT 8347 (AqSynJ12); CECT 8348 (AqSynJ17); CECT 8349 (AqSynJ55) and CECT 8350 (AqSynJ59) were deposited on May 16, 2013.

CECT 8700 (AqSynRMH69): *Lactobacillus reuteri*
CECT 8163 (AqSyn04): *Lactobacillus reuteri*
CECT 8165 (AqSyn06): *Lactobacillus reuteri*
CECT 8164 (AqSyn09): *Enterococcus faecium*

CECT 8166 (AqSyn10): *Enterococcus faecium*
CECT 8347 (AqSynJ12): *Lactobacillus fermentum*
CECT 8348 (AqSynJ17): *Lactobacillus reuteri*
CECT 8349 (AqSynJ55): *Lactobacillus mucosae*
CECT 8350 (AqSynJ59): *Lactobacillus plantarum*

For example, in a preferred embodiment, the composition of the invention comprising the strain deposited at Spanish Type Cultures Collection with deposit number CECT 8700 (AqSynRMH69) further comprises the strain deposited at Spanish Type Cultures Collection with deposit number CECT 8350 (AqSynJ59). The composition may not comprise any further strain.

In a more preferred embodiment, the composition comprises two strains of microorganisms. Preferably, one of the strains is CECT 8700 (AqSynRMH69). Even more preferably, the composition of the invention comprises or, alternatively, consists of two microorganisms, such as two strains. Preferably, the two microorganisms are the strain deposited at Spanish Type Cultures Collection with deposit number CECT 8700 (AqSynRMH69) and the strain deposited at Spanish. Type Cultures Collection with deposit number CECT 8350 (AqSynJ59). In this embodiment, the composition may further comprise other components which are not microorganisms, namely the composition may comprise further components (such as the ones described below), but preferably the composition does not comprise further strains besides CECT 8350 (AqSynJ59) and CECT 8700 (AqSynRMH69).

Accordingly, the composition of the invention may comprise a mixture of microorganisms, wherein the microorganisms belong to the species *Lactobacillus plantarum* and *Lactobacillus reuteri*. Optionally, the composition of the invention may further include at least one microorganism belonging to the genera *Lactobacillus* (preferably with the exception of *Lactobacillus fermentum* CECT 8347 (AqSynJ12)) and *Lactobacillus mucosae* CECT 8349 (AqSynJ55)), *Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*. Optionally, the composition of the invention may further include at least one microorganism belonging to the genera *Lactobacillus* (preferably with the exception of microorganisms belonging to the species *Lactobacillus fermentum* and *Lactobacillus mucosae*) *Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*.

In a preferred embodiment, the composition of the invention comprises a mixture of microorganisms, wherein the mixture consists of at least one strain of *Lactobacillus plantarum* and at least one strain of *Lactobacillus reuteri*. In a more preferred embodiment, the composition of the invention comprises a mixture of microorganisms, wherein the mixture consists of one strain of *Lactobacillus plantarum* and one strain of *Lactobacillus reuteri*. A preferred strain of *Lactobacillus plantarum* is CECT 8350 (AqSynJ59). A preferred strain of *Lactobacillus reuteri* is CECT 8700 (AqSynRMH69). In an even more preferred embodiment, the composition of the invention comprises a mixture of microorganisms, wherein the mixture consists of CECT 8350 (AqSynJ59) and CECT 8700 (AqSynRMH69).

It is believed that different strains may have different actions in the gut, and different strains may therefore act together to provide a beneficial effect.

In one embodiment of the present invention, at least one of the strains comprised in the composition of the invention, such as one, and/or two, and/or three, and/or four and/or five and/or six, and/or seven and/or eight of the strains comprised in the composition, and preferably all of the strains comprised in the composition, are free from antibiotic resistance, namely they are not able to survive after exposure to the appropriate standard antibiotic treatment.

For example, in one embodiment, the composition comprises or, alternatively, consists of CECT 8700 (AqSynRMH69) and CECT 8350 (AqSynJ59) free from antibiotic resistance.

For the purpose of distinguishing resistant from susceptible strains, the European Food Safety Authority (EFSA) Panel on Additives and Products or Substances used in Animal Feed (FEEDAP) defines microbiological cut-off values. Microbiological cut-off values are set by studying the distribution of MICs of the chosen antimicrobials in bacterial populations belonging to a single taxonomical unit (species or genus). The part of the population that clearly deviates from the normal susceptible populations is categorised as resistant. The microbiological cut-off values that may be used for evaluating the antibiotic resistances of the strains of the present invention are the ones defined in the "*Guidance on the assessment of bacterial susceptibility to antimicrobials of human and veterinary importance*", EFSA Panel on Additives and Products or Substances used in Animal Feed (FEEDAP), European Food Safety Authority (EFSA), Parma, Italy. EFSA Journal 2012; 10(6):2740.

An in vitro test of minimal inhibitory concentration (MIC) aimed to evaluate antibiotic resistances may performed for all the strains suggested. The evaluated antibiotics may be the following: Ampicillin, Vancomicin, Gentamicin, Kanamycin, Streptomycin, Eritromycin, Clindamycin, Tetracyclin and Chloranphenicol.

The other ingredient (or other ingredients) which may be present in the composition of the invention is not limited in any way. In a preferred aspect, at least one prebiotic compound is comprised in the composition of the invention, i.e. as other ingredient. In a very broad concept, prebiotics are all those food sources which can be metabolized by probiotics. Preferably prebiotics are non-digestible or poorly digestible by a mammal. Thus, following uptake by the mammal, the non-digestible prebiotics can pass through the small intestine and enter the large intestine to stimulate the growth of the probiotics in this compartment. Prebiotics can thus serve as a food source for probiotics. It is believed that the prebiotics, many of which are non-digestible carbohydrates, promote the growth of probiotics inside the gut. Prebiotics are naturally found for example in onions, whole grains, bananas, garlic, honey, leeks, artichokes, fortified foods and beverages, as well as dietary supplements. Prebiotics are well known in the art and when used in the present invention there is no particular limitation of the prebiotic as such. In preferred embodiments however the at least one prebiotic product in the composition is selected from the following compounds and compositions: non-digestible carbohydrates, beta-glucans, mannan-oligosaccharides, inulin, oligofructose, galactooligosaccharides (GOS), lactulose, lactosucrose, galactotriose, fructo-oligosaccharide (FOS), cellobiose, cellodextrins, cylodextrins, maltitol, lactitol, glycosilsucrose, Vitamin E or a variant thereof (wherein the variants are selected from alfa, beta, gamma, delta tocoferols, tocotrienols and tocomonoenols). Optionally, mannan-oligosaccharides and/or inulin may be preferred. Optionally, mannan-oligosaccharides, beta-glucans and/or inulin may be preferred.

For example, the composition of the present invention may further comprise thickeners and/or complementary feeds/nutrients. For example, the composition of the present invention may comprise one or more thickeners (thickening agents, namely substances which may increase the viscosity of a liquid without substantially changing its other properties, and which may improve the suspension of other ingredients or emulsions which increases the stability of the product), such as polysaccharides (pectin, vegetable gums and/or starched) or proteins. For example, the composition of the present invention further comprises vegetable gums such as alginin, locust bean gum, xanthan gum and/or guar gum, preferably xanthan gum and/or guar gum. For example, the composition may comprise vegetable gums such as xanthan gum and guar gum in an amount of about 0.1-0.5%, preferably about 0.3% w/v (0.3 grams of thickener (e.g., vegetable gums such as xanthan gum and guar gum) in 100 ml.

In addition, the composition of the present invention may comprise complementary feed (nutrients), such as for example milk products, sugars, etc. The composition may comprise skim milk powder in an amount of about 0.5-2% w/v, preferably about 1% w/v. The composition may further comprise sugar (preferably sucrose) in an amount of about 0.1% w/v to 1% w/v, preferably about 0.5% w/v.

In addition, the composition of the present invention may further comprise an infusion solution, such as saline water (water with NaCl). For example, the composition may comprise water with about 0.9% w/v NaCl as infusion solution.

In one embodiment, the composition of the present invention comprises or, alternatively, consists of the following:

| Material | Quantity per 2 ml dose | Concentration per 2 ml dose |
| --- | --- | --- |
| Strain AqSynJ59 -*Lactobacillus plantarum* | 0.076 g | $10^9$ CFU |
| Strain AqSynRMH69-*Lactobacillus reuteri* | | |
| CHEMGEL-56 (Xanthan gum + guar gum) | 0.006 g | 0.3% |
| Skim Milk powder | 0.02 g | 1% |
| Sucrose | 0.01 g | 0.5% |
| Infusion solution (water + 0.9% NaCl) | 2 mL | — |

Concerning the compositions of the invention, which may comprise different strains, any mixing ratio is possible. The mixing ratio is indicated in colony forming units (CFU), which are suitably determined prior to mixing the individual strains. In one embodiment, the ratios of the strains may or may not be equal, such as 1:(0.1-1) for a composition comprising two strains, 1:(0.110):(0.1-10) for a composition comprising three strains, 1:(0.1-10):(0.1-10):(0.1-10) for a composition comprising four strains, and so forth. For example, the ratio in a composition comprising two strains may be from 1:2 to 2:1. In another embodiment, the ratios of the strains are roughly or substantially equal, such as 1:1 for a composition comprising two strains, 1:1:1 for a composition comprising three strains, 1:1:1:1 for a composition comprising four strains, and so forth. The composition can be prepared by mixing the respective bacterial amount (as determined by colony count) of each strain to be incorporated into the composition. The strains to be incorporated may be provided as stocks of individual strains, each one of them for example in the form of a lyophilisate. In the event that different stocks have different concentrations (CFU/g), appropriate amounts (g) of each one are used, so that the desired composition has the desired CFU of each of the strains. Examples thereof are shown below.

In a preferred embodiment, where the composition comprises or, alternatively consists of two strains, the ratios of the strains are roughly or substantially equal, such as 1:1. For example, the composition of the present invention may comprise or, alternative consist of, strain AqSynJ59—*Lactobacillus plantarum* and strain AqSynRMH69-*Lactobacillus reuteri* in a ratio 1:1, such as for example more than or about $5 \times 10^8$ CFU of each of the above strains (e.g., a total of more than or about $10^9$ CFU in the composition).

The present invention also provides the use of the composition of the invention in a method of treating a human and/or an animal. The composition of the invention may thus be used in a method of therapeutic treatment (after the clinical manifestation of the disease (e.g., diarrhoea)) and/or prophylactic treatment (before the clinical manifestation of the disease (e.g., diarrhoea)). Treatment of an animal, a mammal and/or a domestic animal in particular, may be preferred. Preferably, the animal is a non-human animal, and more preferably it is from the suborder Suina (the suborder Suina (also known as Suiformes) is a lineage of mammals that includes the pigs and peccaries of the families Suidae and Tayassuidae). Swine or pig, either wild or domestic, may be particularly preferred. This also includes pigs which live in semi-wild conditions, i.e. races of domestic pigs that live most of the year outdoors and find their own food. The composition may be a composition comprising at least one of the above-described deposited strains. In another embodiment, the composition of the invention may be administered to a human.

The composition of the invention may be used in a method for treating a human or an animal, as described above. This method for treating a human or an animal may be a method for increasing weight of a newborn mammal, preferably a piglet. Additionally and/or alternatively, the method for treating a human or an animal may be a method for promoting growth of a newborn mammal, preferably a piglet. Additionally and/or alternatively, the method for treating a human or an animal may be a method for treating or preventing diarrhoea in a newborn mammal, preferably a piglet. The diarrhoea may be caused by a bacterial infection. The diarrhoea may be due to a non-bacterial infection, such as a viral infection and/or a parasite. The method for treating a human or an animal may be a method for treating or preventing an infection, such as a bacterial infection and/or a viral infection. In addition, the composition of the present invention may be administered before any symptoms are detected, in order to prevent a condition in a human and/or an animal, such as for example diarrhoea and/or an infection, for example a bacterial infection and/or a viral infection.

The composition of the invention may be preferably used in a method for treating an animal. Preferably, the animal is a farm animal, and farm animals include without limitation horses, cattle, chicken and other poultry, swine, sheep, goats. More preferably, the animal is from the suborder Suina, even more preferably a piglet. This method for treating an animal may be a method for increasing weight of a newborn mammal, preferably a piglet. Additionally and/or alternatively, the method for treating an animal may be a method for promoting growth of a newborn mammal, preferably a piglet. Additionally and/or alternatively, the method for treating an animal may be a method for treating or preventing diarrhoea in a newborn mammal, preferably a piglet. The diarrhoea may be caused by a bacterial infection. The diarrhoea may be caused by a viral infection, or by any other cause. In addition, the composition of the present invention may be administered before any symptoms are detected, in order to prevent a condition in an animal, such as for example diarrhoea and/or an infection, such a bacterial and/or a viral infection.

The composition of the present invention may be beneficially administrated to a newborn mammal, preferably a piglet even if no clinical manifestation of the disease (e.g., diarrhoea) has (yet) taken place. For example, the composition of the present invention may be beneficially administrated to healthy newborn mammals, preferably piglets.

The composition of the present invention may be administered to newborn mammals, preferably piglets which:
Show clinical manifestations of diarrhoea.
Do not (yet) show clinical manifestations of diarrhoea but which are infected with bacteria and/or virus which will potentially cause diarrhoea.
Are healthy.

Preferably, the human and/or animal which are being treated with the composition of the present invention are not undergoing any other treatment; preferably, the human and/or animal are not being treated with antibiotics.

Antibiotics are medications used to treat, and/or prevent infections such as bacterial infections.

In a preferred embodiment, the composition of the invention is administered to newborn humans and/or animals (preferably piglets) in an early stage after birth, namely within the first 30 days after birth, preferably within the first 21, 20, 19, 18, 17, 16, 15, 14, 13, 12, 11, 10, 9, 8, 7, 6, 5, 4, 3 or 2 days after birth and most preferably within the first 2 days (48 hours) after birth or within the first 1 day (24 hours) after birth. It is preferably administered at least three times, such as two times or one times. Preferably, the composition of the invention is administered at least one time (such as one time) within the first 48 hours after birth. Preferably, the composition of the invention is administered one time within the first 48 hours after birth, even more preferably within the first 24 hours after birth, such as just (immediately) after birth. The composition of the invention may be administered two times; one within the first day after birth and the second one within the second day after birth.

As described above, at least one (such as one), such as at least two (such as two), such as at least three, such as four or more than four different strains of microorganisms, (being most preferably two), preferably bacteria and more preferably lactic acid bacteria, selected according to at least one, and preferably all three criteria a. to c. as described above, are comprised in the composition of the invention. In the case of the composition for the use in a method for treating a human and/or an animal, as described above, each microorganism, preferably bacteria and more preferably lactic acid bacterium must fulfil at least one of the criteria a. to c. (activity against undesired bacteria; acid tolerance; bile salts tolerance) as described above. Concerning criterium a., the above-referenced minimal inhibition zone is preferably observed for all of undesired bacteria (i) to (iv). Preferably, the microorganisms, preferably bacteria and more preferably lactic acid bacteria comprised in the composition of the present invention should fulfil a plurality (such as a. and b.) and preferably all of the criteria (a. to c.) above. In addition, preferably, at least one (such as one), such as at least two (such as two), such as at least three, such as four or more than four different strains of microorganisms, (being most preferably two), preferably bacteria and more preferably lactic acid bacteria comprised in the composition of the invention (suitable for the use in a method for treating a human and/or an animal) are free from antibiotic resistance, namely they are not able to survive after exposure to the appropriate standard antibiotic treatment. Either a probiotic composition or a synbiotic composition can be used in said method for treating a human and/or an animal (i.e. one comprising at least one prebiotic compound).

The composition of the invention preferably comprises live microorganisms, preferably bacteria.

The present inventors have found that the administration of the composition of the invention in any of its variants at the right time (namely, at an early stage after birth, as described above) has a dramatic effect in the way a newborn human or animal (preferably a piglet) can manage dysbiosis from different aetiologies. For instance, in order for the composition to have better effects in the treatment of a human and/or animal, for example in the treatment or prevention of diarrhoea, the inventors have found that the composition should preferably be administered at an early stage after birth, for example within the first 30 days after birth (more preferably within the first 21, 20, 19, 18, 17, 16, 15, 14, 13, 12, 11, 10, 9, 8, 7, 6, 5, 4, 3 or 2 days after birth and most preferably within the first 2 days after birth or within the first 1 day (24 hours) after birth. Even more preferably, the composition of the invention is administered within the first two days after birth, such as for example once within the first 48 hours after birth, and/or such as for example on the first day after birth (24 hours) and/or on the second day after birth. The composition may (optionally in addition) be administered on the third day after birth. Preferably, the composition of the invention is administered one time within the first 48 hours after birth, even more preferably within the first 24 hours after birth, such as just after birth. Optionally, especially if diarrhoea and/or infection symptoms are observed in the animal and/or human, a second dose of the probiotic composition is administered 24 hours after the first dose.

Any route of administration is suitable, but oral administration may be preferred. Most typically, a dose is given to every animal directly into the mouth to make sure that the animal swallows the dose. Alternatively, the composition may also be provided as a food supplement, i.e. added to the daily feed of the animal.

The composition may be in any form, such as in lyophilized, liquid or nebulized form. If for example lyophilized bacteria are used for making the composition, then said preliminary composition of lyophilized bacteria may be rehydrated, e.g. with sterile isotonic saline solution or with sterile water or with sterile growth medium, so that a final composition with the desired total concentration (CFU/ml) can be obtained.

To provide for easy use, the composition may be in dosed form. For example, each dose may comprise $10^7$ or more, $10^8$ or more, $10^9$ or more, $10^{10}$ or more, $10^{11}$ or more colony forming units (CFU) of microorganisms (preferably bacteria); a dose of $10^9$ or more may be preferred. A dose may have a volume in the range of 0.1 to 100 ml, preferably 0.2 to 50 ml, more preferably 0.5 to 20 ml, more preferably 1.0 to 10 ml, more preferably 1.5 to 5 ml, and even more preferably (substantially) 2 ml. A 2 ml dose with $10^9$ or more CFU may be particularly preferred. In the case where the composition comprises two strains, the 2 mL dose would preferably comprise $5 \cdot 10^8$ CFU of each strain (namely a total of $10^9$ CFU per dose).

Any number of doses may be administered and the skilled person can chose the length of the treatment according to the needs at the respective farm. In a particular embodiment the total number of doses administered to an animal is 10 or less, such as any number selected from the following: 1, 2, 3, 4, 5, 6, 7, 8, 9 10, or any range combining any one of these numbers (except 10) with any one of these number, provided that the second number is higher (e.g. 1 to 3 doses for example).

For example, at least a single dose is administered to an animal within the first 48 hours after birth. For example, a single dose is administered to an animal within the first 48 hours after birth. For example, a single dose is administered to an animal just after birth (within the first 24 hours after birth). Optionally, preferably if the animal shows symptoms of diarrhoea and/or infection, a second dose is administered to the animal 24 hours after the first dose. Optionally a third dose may be subsequently administered 24 hours after the second dose, and so forth.

A total of two doses per animal may be preferred. In a preferred embodiment, a first dose is administered in the first 24 hours after birth (day 1 after birth) and a second dose is administered in the subsequent 24 hours (day 2 after birth). Optionally, these are the only two doses. hi another option, further doses are administered in the following, such as a third dose on the third day after birth, and/or a fourth dose in the fourth day after birth and so forth.

Preferably, the doses comprise each at least two strains. Preferably, the two strains are CECT 8700 (AqSynRMH69) and CECT 8350 (AqSynJ59), and are administered in 2 mL doses, comprising $5·10^8$ CFU of each strain (namely the strains are in a ratio indicated in colony forming units (CFU) of 1:1), within the first 48 hours after birth, such as within the first 24 hours after birth, preferably just after birth. A second and/or third dose may optionally be administered within the first 48 hours after birth and/or on the third day after birth. For example, one dose may be administered just after birth (in the first 24 hours) and optionally a second dose is administered 24 hours after the first dose, namely during the second day after birth, especially if symptoms of diarrhoea and/or infection are observed. A third dose may be optionally administered on the third day after birth. They are preferably administered to mammals, preferably to newborn piglets.

Preferably, the doses comprise each at least two strains. Preferably, the two strains are CECT 8700 (AqSynRMH69) and CECT 8350 (AqSynJ59), and are administered in 2 mL doses, comprising $5·10^8$ CFU of each strain (namely the strains are in a ratio indicated in colony forming units (CFU) of 1:1), on the first and the second day after birth. A third dose may optionally be administered on the third day after birth. They are preferably administered to mammals, preferably to newborn piglets.

The composition of the invention is particularly suitable for treating or preventing a condition in a human and/or an animal, preferably a newborn mammal, as described above, such as diarrhoea, a bacterial infection, a viral infection or dysbiosis. The infection may be or include an infection of the digestive tract. Such infection may be caused by any bacterium, such as e.g. *Escherichia call*, alone or in combination with *Clostridium perfringens* or with *Clostridium difficile*. Other causative factors may include *Salmonella, Listeria monocytogenes, Staphyloccocus aureus*. In some embodiments the condition may be selected from diarrhoea due to bacterial infections (including collibacillosis), *Clostridium difficile* newborn diarrhoea, *Clostridium perfringens* A and C type. Streptococcal meningitis may also be treated. The infection may be caused by any virus, such as rotavirus, coronavirus, norovirus adenovirus and/or astrovirus, preferably by rotavirus and/or coronavirus.

It is also possible to administer the composition to animals suffering from diarrhoea or being at a risk of suffering from diarrhoea, even if a (bacterial and/or viral) infection has not (yet) been proven to be the causative factor for said diarrhoea. Animals being at a risk of suffering from diarrhoea can be seen as those animals living on (or born on) premises on which diarrhoea had been observed during the last 12 months, 6 months, 3 months or 1 month.

The composition of the invention may also be administered before the human and/or animal has any symptoms of diarrhoea and/or of any infection, in order to prevent the diarrhoea and/or the infection.

The skilled person is able to detect symptoms of diarrhoea and/or of any infection in a human and/or animal. For example, the symptoms may be watery diarrhoea, watery/thin (paste-like) faeces, pain, mild systemic signs such as pyrexia, anorexia and/or lethargy, weakness, worsening/deterioration of the general body condition, slimming, etc. Any other symptom indicative of an abnormal behaviour may be indicative of diarrhoea and/or infection.

The composition of the invention may also be administered if the human and/or animal has no symptoms of diarrhoea and/or of infection, namely to healthy human and/or animals.

In a preferred embodiment, the composition of the invention comprises or, alternatively, consists of CECT 8700 (AqSynRMH69) and CECT 8350 (AqSynJ59), and are administered in 2 mL doses comprising $5·10^8$ CFU of each strain to a new born animal, preferably a newborn piglet two times, one in the first day after birth and the other one in the second day after birth (for example 24 hours after the administration of the first dose). The composition may be for use in a method of treating newborn piglets, particularly in a method of treating and/or preventing diarrhoea preferably caused by an infection, such as a bacterial infection, and/or a viral infection. The composition may be also administered to healthy newborn piglets (namely piglets with no symptoms of diarrhoea and/or of infection). In addition, the composition may also be used in a method of increasing weight and/or promoting growth of a new born animal, preferably a newborn piglet.

The inventor's results confirm the advantageous effect of the use of the products and compositions of the invention. As shown in the below proof of concept examples, the mortality percentage was clearly lower than other weeks with just routine antibiotic management (see Examples). Thus, preferably the composition of the invention is administered to animals which are not treated at the same time with antibiotic(s).

The present invention also provides a microorganism, the strain CECT 8700 (AqSynRMH69). It is believed that this strain has probiotic properties, and it may therefore be referred to as probiotic herein. The strain was isolated by the present inventors according to the selection criteria above. CECT refers to Spanish Type Cultures Collection, while the AqSyn numbers in brackets, which can be used synonymously for each of the strains, were allocated to the strains by the present inventors. The bacterium was tested and found to fulfil at least one of criteria a. to c. above.

When finding further strains with beneficial properties according to this invention, it may be sufficient that any such strain, in order to be selected as suitable for the present invention, fulfils at least one of the criteria a. to c. above. The invention also provides a composition comprising at least one, such as one, preferably at least two, such as two, more preferably at least three, such as three, more preferably at least four, such as four, alternatively at least five, such as five, alternatively at least six, such as six, alternatively at least seven, such as seven, alternatively at least eight, such as eight of these strains. It is believed that different strains have different actions in the gut, and different strains may therefore act together to provide a beneficial effect.

Items of the Present Invention (I)

1. A composition comprising at least the strain deposited at Spanish Type Cultures Collection with deposit number CECT 8700 (AqSynRMH69).

2. The composition according to item 1 further comprising at least one strain of microorganisms, wherein each further strain has at least one of the following antimicrobial activities, as evidenced by inhibition zones determined by the spot on lawn assay: (i) 10 mm or more inhibition zone for *Salmonella*, (ii) 9 mm or more inhibition zone for *Listeria monocytogenes*, (iii) 9 mm or more inhibition zone for *Staphyloccocus aureus*, (iv) 10 mm or more inhibition zone for *Escherichia coli*.

3. The composition according to any one of items 1 to 2, wherein the at least one further strain is selected from strains belonging to the genera *Lactobacillus, Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*, 4. The composition according to any one of items 1 to 3, wherein the composition further comprises the strain deposited at Spanish Type Cultures Collection with deposit number CECT 8350 (AqSynJ59).

5. The composition according to item 4, wherein the composition comprises two strains of microorganisms, and wherein the two microorganisms consist of the strain deposited at Spanish Type Cultures Collection with deposit number CECT 8700 (AqSynRMH69) and the strain deposited at Spanish Type Cultures Collection with deposit number CECT 8350 (AqSynJ59).

6. The composition according to any one of items 2 to 5, wherein both strains are present in a ratio indicated in colony forming units (CFU) of approximately from 1:2 to 2:1 in the composition.

7. The composition according to item 6, wherein both strains are present in a ratio indicated in colony forming units (CFU) of approximately 1:1 in the composition.

8. The composition according to any one of items 1 to 7, wherein at least one strain, and preferably all the strains comprised in the composition are free from antibiotic resistance.

9. The composition according to any one of items 1 to 8, wherein at least one strain, and preferably all strains comprised in the composition are able to retain essentially the same viability during 3 hours of incubation at pH 3.5.

10. The composition according to any one of items 1 to 9, wherein at least one strain, and preferably all strains comprised in the composition are able to retain essentially the same viability during 4 hours of incubation in presence of 0.45% bile extract.

11. The composition according to any one of items 1 to 10, wherein at least one strain, and preferably all strains comprised in the composition have all of the following antimicrobial activities, as evidenced by inhibition zones determined by the spot on lawn assay: (i) 10 mm or more inhibition zone for *Salmonella*, (ii) 9 mm or more inhibition zone for *Listeria monocytogenes*, (iii) 9 mm or more inhibition zone for *Staphylococcus aureus*, (iv) 10 mm or more inhibition zone for *Escherichia coli*.

12. The composition according to any one of items 1 to 11, for use in a method for treating a human and/or an animal.

13. The composition according to claim 12, for use in a method for treating an animal.

14. A composition comprising a mixture of microorganisms, wherein the microorganisms belong to the species *Lactobacillus plantarum* and *Lactobacillus reuteri*, and optionally including at least one microorganism belonging to the genera *Lactobacillus, Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*, for use in a method for treating a human or animal.

15. A composition comprising a mixture of microorganisms, wherein the microorganisms belong to the species *Lactobacillus plantarum* and *Lactobacillus reuteri*, and optionally including at least one microorganism belonging to the genera *Lactobacillus* (with the exception of the following microorganisms: CECT 8347 (AqSynJ12) and CECT 8349 (AqSynJ55)), *Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*, for use in a method for treating a human or animal.

16. A composition comprising a mixture of microorganisms, wherein the microorganisms belong to the species *Lactobacillus plantarum* and *Lactobacillus reuteri*, and optionally including at least one microorganism belonging to the genera *Lactobacillus* (with the exception of microorganisms belonging to the species *Lactobacillus fermentum* and *Lactobacillus mucosae*) *Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*, for use in a method for treating a human or animal.

17. The composition for use according to any one of claims 12-16, wherein the mixture of microorganisms consists of microorganisms belonging to the species *Lactobacillus plantarum* and *Lactobacillus reuteri*.

18. The composition for use according to any one of items 12-17, wherein at least one strain, and preferably all strains have at least one of the following antimicrobial activities, as evidenced by inhibition zones determined by the spot on lawn assay: (i) 10 mm or more inhibition zone for *Salmonella*, (ii) 9 mm or more inhibition zone for *Listeria monocytogenes*, (iii) 9 mm or more inhibition zone for *Staphyloccocus aureus*, (iv) 10 mm or more inhibition zone for *Escherichia coli*.

19. The composition for use according to any one of items 12 to 18, wherein at least one strain, and preferably all the strains comprised in the composition are free from antibiotic resistance.

20. The composition for use according to any one of items 12 to 19, wherein at least one strain, and preferably all strains comprised in the composition are able to retain essentially the same viability during 3 hours of incubation at pH 3.5.

21. The composition for use according to any one of items 12 to 20, wherein at least one strain, and preferably all strains comprised in the composition are able to retain essentially the same viability during 4 hours of incubation in presence of 0.45% bile extract.

22. The composition for use according to any one of items 12 to 21, wherein the composition is administered to the human or animal within the first 30 days after birth.

23. The composition for use according to item 22, wherein the composition is administered to the human or animal within the first 14 days after birth.

24. The composition for use according to item 23, wherein the composition is administered to the human or animal within the first 7 days after birth.

25. The composition for use according to item 24, wherein the composition is administered to the human or animal within the first 2 days after birth.

26. The composition for use according to any one of items 12 to 25, wherein the method is for treating or preventing diarrhoea.

27. The composition for use according to item 26, wherein the diarrhoea is caused by an infection, such as a bacterial and/or viral infection, preferably by a bacterial infection.

28. The composition for use according to any one of items 12 to 27, wherein the method is for treating an animal of the suborder Suina, dogs, cats, horses, cattle, poultry, sheep and/or goats.

29. The composition according to any one of items 1 to 11, or the composition for use according to any one of items 12 to 28, wherein the composition additionally comprises at least one prebiotic product.

30. The composition according to item 29, wherein the at least one prebiotic product is selected from the following compounds and compositions: beta-glucans, mannan-oligosaccharides, inulin, oligofructose, galactooligosaccharides (GOS), lactulose, lactosucrose, galactotriose, fructooligosaccharide (FOS), cellobiose, cellodextrins, cylodextrins, maltitol, lactitol, glycosilsucrose, Vitamin E or a variant thereof (wherein the variants are selected from alfa, beta, gamma, delta tocoferols, tocotrienols and tocomonoenols) whereby mannan-oligosaccharides, beta-glucans and/or inulin are preferred.

31. The composition according to any one of items 1 to 11, or the composition for use according to any one of items 12 to 30, wherein the composition is for oral administration.

32. The composition according to any one of items 1 to 11, or the composition for use according to any one of items 12 to 31, wherein the composition is in lyophilized, liquid or nebulized form.

33. The composition according to any one of items 1 to 11, or the composition for use according to any one of items 12 to 32, wherein the composition is provided in dosage form, and wherein each dose comprises about $10^9$ colony forming units (CPU).

34. The composition according to any one of items 1 to 11, or the composition for use according to any one of items 12 to 33, wherein the composition is administered in one single dose.

35. The composition according to item 34, wherein the composition is administered in the first 48 hours after birth.

36. The composition according to item 35, wherein the composition is administered in the first 24 hours after birth.

37. The composition according to item 36, wherein the composition is administered just after birth.

38. The composition according to any one of items 1 to 11, or the composition for use according to any one of items 12 to 33, wherein the composition is administered in two doses.

39. The composition according to item 38, wherein the first dose is administered in the first 24 hours after birth and the second dose is administered in the subsequent 24 hours.

40. The composition according to item 39, wherein the second dose is administered only if the animal and/or human shows diarrhoea and/or infection symptoms (such as for example watery diarrhoea, watery/thin (paste-like) faeces, pain and/or mild systemic signs such as pyrexia, anorexia and/or lethargy, weakness, worsening/deterioration of the general body condition, slimming, etc.).

41. The composition according to any one of items 1 to 11, or the composition for use according to any one of items 12 to 40, wherein the composition is used in the treatment or prevention of a bacterial infection, such as diarrhoea caused by bacterial infections (including collibacilosis), *Clostridium difficile* newborn diarrhoea, *Clostridium perfringens* A and C type.

42. A strain deposited at Spanish Type Cultures Collection with deposit number CECT 8700 (AqSynRMH69).

Items of the Present Invention (I)

1. A composition comprising at least the strain deposited at Spanish Type Cultures Collection with deposit number CECT 8700 (AqSynRMH69).

2. The composition according to item 1 further comprising at least one strain of microorganisms, wherein each further strain has at least one of the following antimicrobial activities, as evidenced by inhibition zones determined by the spot on lawn assay: (i) 10 mm or more inhibition zone for *Salmonella*, (ii) 9 mm or more inhibition zone for *Listeria monocytogenes*, (iii) 9 mm or more inhibition zone for *Staphyloccocus aureus*, (iv) 10 mm or more inhibition zone for *Escherichia coli*.

3. The composition according to item 2, wherein the at least one further strain is selected from strains belonging to the genera *Lactobacillus, Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*.

4. The composition according to any one of items 1 to 3, wherein the composition further comprises the strain deposited at Spanish Type Cultures Collection with deposit number CECT 8350 (AqSynJ159).

5. The composition according to item 4, wherein the composition comprises two strains of microorganisms, and wherein the two microorganisms are the strain deposited at Spanish Type Cultures Collection with deposit number CECT 8700 (AqSynRMH69) and the strain deposited at Spanish Type Cultures Collection with deposit number CECT 8350 (AqSynJ59).

6. The composition according to item 5, wherein both strains are present in a ratio (indicated in colony forming units (CFU)) of from 2:1 to 1:2 in the composition.

7. The composition according to any one of items 1 to 6, wherein at least one strain, and preferably all the strains comprised in the composition are free from antibiotic resistance.

8. The composition according to any one of items 1 to 7, wherein at least one strain, and preferably all strains comprised in the composition are able to retain essentially the same viability during 3 hours of incubation at pH 3.5.

9. The composition according to any one of items 1 to 8, wherein at least one strain, and preferably all strains comprised in the composition are able to retain essentially the same viability during 4 hours of incubation in presence of 0.45% bile extract.

10. The composition according to any one of items 1 to 9, wherein at least one strain, and preferably all strains comprised in the composition have all of the following antimicrobial activities, as evidenced by inhibition zones determined by the spot on lawn assay: (i) 10 mm or more inhibition zone for *Salmonella*, (ii) 9 mm or more inhibition zone for *Listeria monocytogenes*, (iii) 9 mm or more inhibition zone for *Staphyloccocus aureus*, (iv) 10 or more inhibition zone for *Escherichia coli*.

11. The composition according to any one of items 1 to 10, for use in a method for treating an animal and/or a human.

12. A composition comprising a mixture of microorganisms, wherein the microorganisms belong to the species *Lactobacillus plantarum* and *Lactobacillus reuteri*, and optionally including at least one microorganism belonging to the genera *Lactobacillus* (with the exception of microorganisms *Lactobacillus Fermentum* CECT 8347 (AqSynJ12) and *Lactobacillus mucosae* CECT 8349 (AqSynJ55)) *Leuconostoc, Pediococcus, Lactococcus, Streptococcus Aerococcus, Carnobacterium, Enterococcus, Oenococcus, Sporolactobacillus, Tetragenococcus, Vagococcus* and/or *Weisella*, for use in a method for treating an animal and/or a human.

13. The composition for use according to any one of items 11 to 12, wherein the method is for treating or preventing diarrhoea.

14. The composition according to any one of items 1 to 10, or the composition for use according to any one of claims 11 to 13, wherein the composition is administered at least in one dose within the first 48 hours after birth.

15. A strain deposited at Spanish Type Cultures Collection with deposit number CECT 8700 (AqSynRMH69).

EXAMPLES

Example 1

Material and Methods

MRS Medium: MRS Medium recipe was prepared according to the recipe obtained from Spanish Collection of Type Cultures (CECT; www.cect.org) as follows: Peptone 10.0 g, Beef extract 10.0 g, Yeast extract 5.0 g, Glucose 20.0 g, Ammonium citrate 2.00 g, Sodium acetate 5.00 g, $MgSO_4.7H_2O$ 0.20 g, $MnSO_4.H_2O$ 0.05 g, $K_2HPO_4$ 2.00 g, [Agar powder (only for solid media) 15 g,] Distilled water 1 L.

BHI (Brain Heart Infusion) Medium recipe was prepared according to the recipe obtained from Spanish collection of type cultures (CECT; www.cect.org) as follows: Calf brain infusion solids 12.5 g, Beef heart infusion solids 5.0 g, proteose peptone 10.0 g, Glucose 2.0 g, NaCl 5.0 g, $HNa_2PO_4$ 2.5 g, Distilled water 1 L, [Agar powder (only for solid media) 15 g].

Antibiotic treatment: Typically, each pig farm treats newborn piglets with antibiotics and possibly an iron supplement. Generally each pig farm has a different "standard" treatment for their animals (they usually inject an antibiotic dose and iron supplementation by birth). In the experiments below, the standard treatment of the respective farm was used. Antibiotics are generally also used sporadically by diarrhoea, limps, respiratory symptoms and many other facts daily without a full established protocol in piglets.

Example 1 A: Origin of the Strains

Bacterial strains were isolated and identified as follows.
The isolation of CECT 8350 (AqSynJ59) and CECT 8700 (AqSynRMH69) bacterial strains was made from intestinal wall washes of piglet intestine.

Samples were grown aerobically and anaerobically in De Man, Rogosa, Sharpe (MRS) agar plates for 24 hours at 37° C., and Gram positive, Catalase negative colonies of different morphologies were isolated. All colonies belonged to bacterial strains. Each isolated strain was amplified by PCR using PCR primers targeting the 16S/23S rRNA spacer region as described by Berthier and Ehrlich, 1998. FEMS Microbiology Letters 161: 97-106.

After amplification and electrophoresis, clearly differentiated bands were purified and sequenced. By sequencing the strains were allocated to the bacterial species.

1.1 Characterisation and Selection of the Strains
1. *Lactobacillus plantarum* (AqSynJ59)
2. *Lactobacillus reuteri* (AqSynRMH69)

In vitro tests following criteria a. to c., described above under "selection in vitro tests", revealed two strains with particularly beneficial properties.

a. Inhibition against different pathogens: selected strains show an antimicrobial activity evidenced by at least one of the following inhibition zones: 10 mm or more for *Salmonella,* 9 mm or more for *Listeria monocytogenes,* 9 mm or more for *Staphyloccocus aureus* and 10 mm or more for *Escherichia coli.*

The results for AqSynJ59 and AqSynRMH69 are listed Belo

|   |   | AqSynJ59 | AqSynRMH69 |
|---|---|---|---|
| a. | (i) *Salmonella enterica* serotype Typhimurium inhibition zone [mm] | 13 | 35 |
| a. | (ii) *Listeria monocytogenes* inhibition zone [mm] | 13 | 16 |
| a. | (iii) *Staphyloccocus aureus* inhibition zone [mm] | 9 | 33 |
| a. | (iv) *Escherichia coli* inhibition zone [mm] | 21 | 35 |
| b. | acid tolerant (yes/no) | yes | yes |
| c. | bile salt tolerant (yes/no) | yes | yes |

As can be seen in the above Table, the selected strains from piglet intestine fulfil the selection criteria a. to c. as described above.

b. pH resistance: both strains are able to retain essentially the same viability during 3 hours of incubation at pH=3.5.

c. Bile salt resistance. Both strains are able to retain essentially the same viability during 4 hours of incubation in presence of 0.45% bile extract.

Moreover, the above-identified strains are free from antibiotic resistance.

An in vitro test of minimal inhibitory concentration (MIC) aimed to evaluate antibiotic resistances was performed for the above strains (AqSynJ59 and AqSynRMH69). The evaluated antibiotics were the following:

Ampicillin, Vancomicin, Gentamicin, Kanamycin, Streptomycin, Clindamycin, Tetracyclin and Chloranphenicol.

The microbiological cut-off values that were used for evaluating the antibiotic resistances of the strains of the present invention are the ones defined in the "Guidance on the assessment of bacterial susceptibility to antimicrobials of human and veterinary importance", EFSA Panel on Additives and Products or Substances used in Animal Feed (FEEDAP), European Food Safety Authority (EFSA), Parma, Italy. EFSA Journal 2012; 10(6):2740.

Resistance to EFSA Cut-off Values Antibiotics in Comparison with MIC Results of Each Bacteria:

|   | EFSA (2012) | AqSynJ59 strain | |
|---|---|---|---|
| Antibiotic | values | LSM | Category |
| Ampicillin | 2 | 0.125 | S* |
| Vancomycin | nr | 512 | R** |
| Gentamicin | 16 | 1 | S |
| Kanamycin | 64 | 64 | S |
| Streptomycin | nr | 32 | — |
| Clinidamycin | 1 | 0.125 | S |

-continued

|  | EFSA (2012) values | AqSynJ59 strain | |
|---|---|---|---|
| Antibiotic |  | LSM | Category |
| Tetracycline | 32 | 4 | S |
| Chloramphenicol | 8 | 2 | S |

*Sensible
**Resistant

|  | EFSA (2012) values | AqSynRMH69 strain | |
|---|---|---|---|
| Antibiotic |  | LSM | Category |
| Ampicillin | 2 | 0.25 | S |
| Vancomycin | nr | 512 | R |
| Gentamicin | 8 | 2 | S |
| Kanamycin | 64 | 64 | S |
| Streptomycin | 64 | 32 | S |
| Clindamycin | 1 | 0.125 | S |
| Tetracycline | 16 | 4 | S |
| Chloramphenicol | 4 | 2 | S |

*: Sensible
**: Resistant

LSM=LAB susceptibility test medium consisted in a mixture of IST (Oxoid laboratories) broth (90%) and MRS broth (10%) adjusted to pH 6.7.

Both strains can be considered as non-resistant for the by EFSA recommended antibiotics, therefore they can be use as additives for "food producing" animal feed.

Example 1B: Preparation of a Probiotic Composition According to the Invention

The strains CECT 8350 (AqSynJ59) and CECT 8700 (AqSynRMH169), which fulfil the criteria a. to c., as described in the description and as evidenced above, were included in a probiotic composition and were tested in a field trial.

Each of the strains AqSynJ59 and AqSynRMH69 was grown in MRS broth culture by fermentation, harvested and lyophilized. Viability of the final product was checked by colony count.

Composition was prepared containing all two of these strains. The following composition was prepared:
Composition: ($5\times10^8$ CFU of each strain in 2 ml)

| Components | Quantity per 2 ml dose |
|---|---|
| AqSynJ59: Lactobacillus plantarum | 0.0024 g |
| AqSynRMH69: Lactobacillus reuteri | 0.0052 g |

All strains were used in lyophilized form.

The composition was prepared by mixing the same bacterial amount (as determined by colony count (respective values in g indicated above) of each strain to be incorporated into the composition and the so obtained composition was rehydrated with isotonic saline solution, so that a final composition containing $10^9$ CFU (total of all strains contained therein) in a 2 ml dose was obtained.

Example 1C: Field Test

Newborn piglet's diarrhoea was detected in a North Spain pig producing farm where the two strains product was tested.

The farm basic production unit is the "birth unit". Each birth unit is composed by 24 litters. In the experiment, 12 of the litters were managed under standard farm conditions (control group, which require the use of antibiotics and nutrient compositions to treat piglets in a litter which have shown signs of diarrhea). The other 12 litters were treated with Aquilón's probiotic composition alone, with no further use of antibiotics in case of diarrhoea (all the piglets were orally administered with one dose of the composition (2 ml) as described above on the first day after birth (just after birth). A second dose (2 ml) of the composition was administered on the second day after birth (after 24 hours of the administration of the first dose) only to those animals of the group that showed symptoms of diarrhea). The animals receiving the probiotic composition did not received antibiotics at any moment (although they did received a treatment consisting in the addition of nutrients to the diet the same as the standard managed animals (control group) in case they showed symptoms of diarrhoea). The animals were controlled from birth to day 20 of life.

The probiotic composition used in this trial was a mixture of two Lactobacillus strains, AqSynJ59: Lactobacillus plantarum and AqSynRMH69: Lactobacillus reuteri, containing $10^9$ CFU per 2 mL dose ($5\times10^8$ CFU of each strain), as described above.

The treatment of the control group was with antibiotics, namely an IM injection of amoxicillin in a 5 mg per kg dose, injected during symptoms observation. The diarrhoeic piglets in this control group were receiving this treatment once per day during the days they showed diarrhoea, whereas the diarrhoeic animals in the group receiving Aquilón's probiotic composition (as described above) were not treated with antibiotics at any moment.

Experimental Design

A. Number of live births per litter

B. Deaths after birth.

C. Diarrheas: they are counted on a per litter basis, with the following criteria for scoring:

0.—Less that <25% animals infected: there are no apparent signs of dirty animals in the perianal zone, and no soft feces are observed in the floor or walls.

1.—Some diarrheas: some dirty animal is observed occasionally in the litter, some soft feces in the floor.

2.—The majority of the animals (>75%) show diarrheas and altered physical estate, dirty animals and soft feces in the floor.

D. Treatments: piglets per litter and days that they receive treatment (antibiotics, nutrients, carbon, rehydration, etc.).

Summary of Results

|  | Control group | Probiotic composition group |
|---|---|---|
| Average weight at weaning (kg) | 5.06 | 5.38 |
| Total days of any treatment (oral or abdominal rehydration with physiological infusion (probiotic group), oral or abdominal rehydration with. physiological infusion and antibiotics (control group)) | 34 | 6 |
| Total days of antibiotic treatment | 31 | 0 |
| Deaths caused by diarrhea | 7 | 3 |
| Mortality (%) | 14.11 | 10.43 |

|  | Control group | Probiotic composition group |
|---|---|---|
| Aggregated days with moderate diarrhea | 24 | 10 |
| Aggregated days with severe diarrhea | 10 | 5 |
| Treatment index per litter * | 31.17 | 1.67 |

* Treatment index per litter = (treated litters × days treated/12)

Conclusions:

The tested composition is better than standard practice to prevent and treat piglet diarrhea:

a) Substituted in full the need of antibiotics b) Reduced the need of non-antibiotic accessory treatments c) Reduced the incidence of overall diarrhea d) Reduced the incidence of severe diarrhea e) Reduced the incidence of death caused by diarrhea f) Improved the average weight at weaning g) Reduced in a very significant way the economic impact of diarrhea epidemics under standard management conditions in a commercial exploitation (more kg per animals, less deaths, less cost of treatment, less environmental impact, less handling time).

Example 2

Materials and method of Example 2, as well as the origin of the strains are the same as described above in Example 1 ("Materials and Methods" and "Example 1 A: Origin of the strains").

Example 2 A: Preparation of a Probiotic Composition According to the Invention

The strains CECT 8350 (AqSynJ59) and CECT 8700 (AqSynRMH69), which fulfil the criteria a. to c., as described in the description and as evidenced above (in "Example 1 A: Origin of the strains"), were included in a probiotic composition and were tested in a field trial.

Each of the strains AqSynJ59 and AqSynRMH69 was grown in MRS broth culture by fermentation, harvested and lyophilized. Viability of the final product was checked by colony count.

The composition was prepared containing all two of these strains. The following composition was prepared ("AQ1202-PigLife" or "PigLife" or "AQ1202"):

| Material | Concentration per 2 ml dose | Effect |
|---|---|---|
| Lactobacillus plantarum (CECT 8350) Lactobacillus reuteri (CECT 8700) | ≥$10^9$ CFU (about 5 × $10^8$ CFU of each strain) | Probiotic |
| Xanthan gum + guar gum | 0.3% w/v | Thickener |

Complementary Feed:

| Material | Concentration per dose | Effect |
|---|---|---|
| Skim Milk powder | 1% w/v | Feed/nutrients |
| Sacarose | 0.5% w/v | Feed/nutrients |
| Infusion solution (water + 0.9% w/v NaCl) | 2 ml | Excipient/diluent |

The product (which is given the name of "AQ1202-PigLife", also referred to as "PigLife" or "AQ1202") consists on a freeze-dried mixture of two acid lactic bacteria and different feed substances to define an oral suspension for newborn piglets. The product was mixed in Aquilón's facilities and package in 100 ml vials. This preparation is intended to be eluted in 100 ml infusion solution just before use.

The composition was prepared by mixing the same bacterial amount (as determined by colony count (respective values in CFU indicated above) of each strain to be incorporated into the composition and the so obtained composition was rehydrated with isotonic saline solution, so that a final composition containing $10^9$ CFU (total of all strains contained therein) in a 2 ml dose was obtained.

Example 2 B: Field Test

The aim of this example is to evaluate the use of a probiotic composition according to the invention in piglets after birth, when the piglets particularly vulnerable to dysbiosis and diarrhoea.

The two strains product ("AQ1202-PigLife" or "PigLife") was tested in commercial farms (5 in total) with diarrhoea sporadic outbreaks of varied (known or unknown) aetiologies. The commercial farms were placed in different locations in Spain (Aragón, Castilla y León, Cataluña). All of them harbor intensive pig farming systems, including insemination programs, management of pregnant sows, farrowing and weaning units. Some of them include transition stalls for the animals before their transfer to the fattening unit. The experiments were performed under an official license covering the use of an experimental zootechnical additive in field trials.

Animals Groups:

Probiotic treatment group (AQ1202-PigLife)

Control group (no treatment—no manipulation)

After farrowing (first day of life), all piglets in the treatment group received orally a 2 ml dose of the probiotic composition AQ1202-PigLife (AQ1202). Data were recorded from farrowing to day 20.

The following was evaluated;

Evaluation of zootechnical parameters

Number of piglets born: total born and born alive (mortality-weaned piglets)

Piglets weight (when possible)

Faeces evaluation

0: Normal faeces

1: Mild diarrhoea; some diarrhoea cases appear in the litter

2: Severe diarrhoea; most of the piglets affected with diarrhoea

Treatment evaluation: record of treated litters and sows.

Farms 1 to 4

| Farm | Total observed |
|---|---|
| Farm 1 | 24 |
| Farm 2 | 38 |
| Farm 3.1 | 58 |
| Farm 3.2 | 58 |
| Farm 4 | 61 |

In Farm 3, two different farrowing batches of litters were observed:
Experiment 1: October 2014 (Farm 3.1)
Experiment 2: May 2015 (Farm 3.2)
Data of 135 control and 104 PigLife-treated litters were recorded in these studies.
A total of 1710 control and 1136 treated piglets were observed from farrowing to day 20.
In Farms 1 to 4, the diarrhoea was found to be antibiotic-responsive, namely diarrhoea of bacterial origin.

Mortality (%) (general mortality, including diarrhoea and crushed piglets)

| Group/Farm | Control | AQ1202 |
|---|---|---|
| Farm 1 | 14.1 | 9.9 |
| Farm 2 | 13.2 | 9.9 |
| Farm 3.1 | 19.3 | 14.7 |
| Farm 3.2 | 12.3 | 11.7 |
| Farm 4 | 16.31 | 3.68 |

Figure 2:
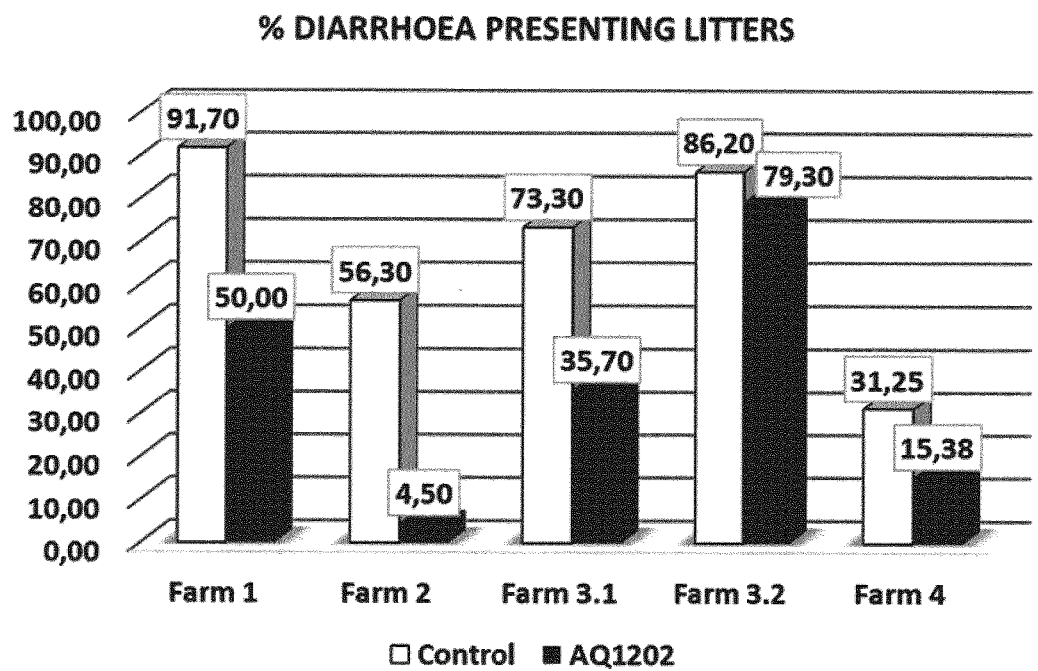
FIG. 2: % of diarrhoea presenting litters.

Diarrhoea (see also FIG. 2)

| | % diarrhoea presenting litters | | Mean of diarrhoea (days) in diarrhoea presenting litters | |
|---|---|---|---|---|
| Group/Farm | Control | AQ1202 | Control | AQ1202 |
| Farm 1 | 91.7 | 50.0 | 3.1 ± 1.8 | 2.5 ± 2.1 |
| Farm 2 | 56.3 | 4.5 | 2.7 ± 1.8 | 2* |
| Farm 3.1 | 73.3 | 35.7 | 2.1 ± 1.1 | 2.8 ± 1.8 |
| Farm 3.2 | 86.2 | 79.3 | 3.2 ± 1.6 | 2.5 ± 1.8 |
| Farm 4 | 31.25 | 15.38 | 1.2 ± 0.8 | 1 ± 0 |

*just one litter with a two days length diarrhoea

Treatments
Farm 1
Affected litters were treated with Amoxicillin+Lincomicin, etiological treatment (mothers) and Tiamulin+colistin (Colimutina, SP Veterinaria)+oral infusion solution, symptomatic treatment in piglets.
Farm 2
The antibiotic used was Enrofloxacin for mothers (it will be released to the piglets by milk), piglets or for both of them. Oral re-hydration and mineral carbon was administered to affected piglets.
Farm 3
In diarrhoea cases within the litters, affected piglets were treated with Enrofloxacin (Alsir, Norvet). Mothers were treated with Marbofloxacin (Marbocyl, Vétoquinol). Colimicin+Infusion solution for symptomatic piglets.
Farm 4
Sows of diarrhoea presenting litters were treated with Enrofloxacin. Treatment could last three days if it was necessary. As prophylaxis, one dose of Ceftiofur (Naxcel, Zoetis) was applied to all piglets in this farm at the first day of life.

The administrated doses were as follows:
Amoxicilin: 15 mg/kg, intramuscular (IM) injection
Lincomicin: 5-10 mg/kg in drinking water
Enrofloxacin; 2.5 mg/kg intramuscular injection
Marbofloxacin: 2 mg/kg intramuscular injection
Colimicin: 0.5 g/liter (drinking water)
Ceftioffir: 5 mg/kg, intramuscular injection
Colimutina: 0.156 mg sodium colistimethate+12.35 mg tiamuline hydrogen fumarate/kg; 0.1 ml/kg intramuscular injection.

Figure 3:
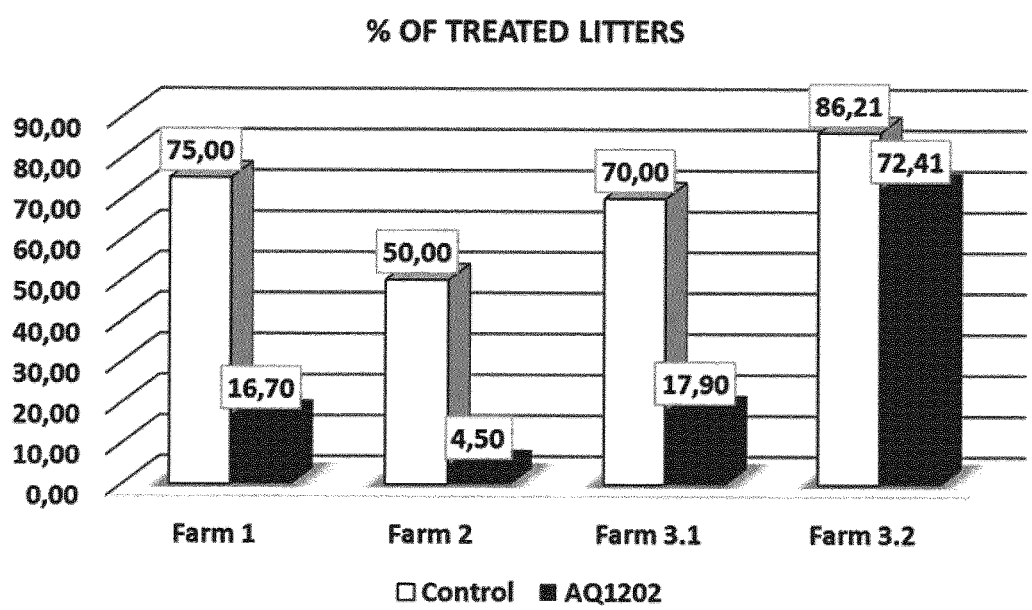
FIG. 3: % of treated litters.

The results are shown in the table below and FIG. 3:

| | % of treated litters | | Mean of treatments length (days) in treated litters Group | |
|---|---|---|---|---|
| Farm | Control | AQ1202 | Control | AQ1202 |
| Farm 1 | 75 | 16.7 | 3.2 ± 1.3 | 2.9 ± 1.2 |
| Farm 2 | 50 | 4.5 | 1.1 ± 0.4 | 1* |
| Farm 3.1 | 70 | 17.9 | 2.76 ± 1 | 2.6 ± 0.5 |
| Farm 3.2 | 86.21 | 72.41 | 3.2 ± 1.3 | 2.9 ± 1.2 |

*Only one litter treated once

Conclusions of Farms 1 to 4
The probiotic composition according to the invention (AQ1202) reduces mortality in farms with persistent diarrhoea episodes (caused by bacterial infection in the case of farms 1-4), as it can be seen from the above table and FIG. 2. The administration of this composition reduces the need of treatments, including antibiotics. The above table and FIG. 3 show the reduced percentage of treated litters (including the treatment with antibiotics) which were taking the probiotic composition according to the invention (AQ1202).
Farm 5
In Farm 5, the diarrhea did not have a bacterial origin. The diarrhea was not responsive to antibiotic treatment. Finally, it was diagnosed a rotavirus infection, which was the cause of the diarrhoea of the newborn piglets, according to the diagnosis reported by the farmer.

This experiment was carried out in a commercial pig farm located in Aragóm (Spain) with a population of 750 breeding sows.

Since early January 2014, the farm was affected by persistent episodes of newborn piglets' diarrhoea, achieving rates of 95% of affected litters by May that year. The mortality rates were increasing until affecting over 35% of born alive piglets. There was a huge use of antibiotic treatment against Enterobacteriaceae and *Clostridium* for more than 6 months with scarce results.

Once transmissible gastroenteritis and epidemic pig diarrhoea (porcine epidemic diarrhoea, Coronaviruses) were discarded as the aetiology of the diarrhoea, the clinical diagnosis was Swine Rotavirus. Accordingly, the diarrhoea in Farm 5 was caused by viral infection, by Swine Rotavirus infection.

The rotavirus infection was confirmed by PCR diagnostic by an external diagnostic laboratory (GSP laboratory, Catalonia, Spain). Due to the high rates of diarrhoea observed in the herd and the low success of the first treatments, the farmer decided to systematically administrate the product (the composition according to the present invention, AQ1202) to all piglets, from May to December 2014.

Since the treatment was introduced, the mortality was reduced to 5%, and the incidence of diarrhoea was reduced to 20% of the litters.

The results are shown below.

Treatments:

In Case of Diarrhea:
- CARBOVET (the product Carbovet® is a thermo-structured (non-activated) vegetal charcoal made from specially selected French oak.
- SUEROMIN (Intraperitoneal re hydration with hypertonic infusion; composition: Glucose 25 g, Fructose 25 g, Chloride 2.62 g, Sodium 1.57 g, Potassium 80 mg, Magnesium 20 mg, Calcium 40 mg; excipient q.s. 1000 ml)

To all Animals:
- AQ1202-PigLife
- 1/5-30/6: 1-2 doses per piglet
- 1/7-31/12: 3 doses per piglet
- Iron: One dose (about 150 mg, intramuscular) per piglet, at any one of day 3 to 8 of life.

The observation of 983 litters (from May to December 2014) was reported in this study, from May to December 2014 (see table below). All piglets in each litter were treated with AQ1202—PigLife (the composition according to the invention).

| Month | Number of reported litters | Percentaje of weaned pigglets | Mean of treatments** | Percentaje of treated* litters |
|---|---|---|---|---|
| May | 115 | 76.6 | 3.08 | 92.2 |
| June | 129 | 81.3 | 2.15 | 85.3 |
| July | 177 | 82.7 | 1.06 | 68.9 |
| August | 144 | 78 | 0.87 | 47.9 |
| September | 152 | 75.7 | 0.87 | 48.7 |
| October | 143 | 82.7 | 0.36 | 19.6 |
| November | 51 | 81.7 | 0.06 | 3.9 |
| December | 72 | 81.9 | 0 | 0 |

*Carbovet and/or Sueromin
**One treatment = 1 dose of Carbovet and/or Sueromin
Carbovet: 10 g/animal, via oral
Sueromin: from 20 to 80 ml/kg via intraperitoneal or subcutaneous The probiotic composition was administered to all piglets within the litters. The percentage of treated litters, which is directly related with diarrhoea observation in the animals, felt from 95% to 5% during continuous application of the probiotic composition according to the present invention (AQ1202—PigLife). Carbovet and Sueromin (symptomatic treatments) were administered only to weak and diarrheic animals. A rising tendency was observed in the percentage of weaned piglets. The farmer observed up to approx. 0.7% more weaned piglets per litter since the probiotic composition was administered.

The invention claimed is:

1. A method for treating or preventing diarrhea caused by a viral infection in a subject in need thereof, comprising administering to said subject a composition comprising a *Lactobacillus reuteri* bacterial strain deposited at the Spanish Type Cultures Collection on Sep. 10, 2014 under deposit number CECT 8700 (AqSynRMH69).

2. The method of claim 1, wherein the composition further comprises at least one additional bacterial strain, wherein the bacterial strain has at least one of the following antimicrobial activities, as evidenced by inhibition zones determined by the spot on lawn assay: (i) a 10 mm or greater inhibition zone for *Salmonella*, (ii) a 9 mm or greater inhibition zone for *Listeria monocytogenes*, (iii) a 9 mm or greater inhibition zone for *Staphyloccocus aureus*, or (iv) a 10 mm or greater inhibition zone for *Escherichia coli*.

3. The method of claim 2, wherein the at least one additional bacterial strain belongs to a genus selected from the group consisting of *Lactobacillus, Leuconostoc, Pediococcus, Lactococcus, Streptococcus Aerococcus, Carnobacterium, Enterococcus, Oenococcus, Sporolactobacillus, Tetragenococcus, Vagococcus* and *Weisella*.

4. The method of claim 1, wherein the composition further comprises a *Lactobacillus plantarum* bacterial strain deposited at Spanish Type Cultures Collection on May 16, 2013 under deposit number CECT 8350 (AqSynJ59).

5. The method of claim 4, wherein the composition comprises only two bacterial strains, and wherein the two bacterial strains are the bacterial strain AqSynRMH69 and the bacterial strain AqSynJ59.

6. The method of claim 5, wherein the bacterial strain AqSynRMH69 and the bacterial strain AqSynJ59 are present in the composition at a ratio of AqSynRMH69:AqSynJ59 of from 2:1 to 1:2 as measured by colony forming units (CFU).

7. The method of claim 2, wherein at least one bacterial strain at least one strain, and comprised in the composition is free from antibiotic resistance.

8. The method of claim 2, wherein at least one bacterial strain comprised in the composition retains essentially the same viability after a 3 hour incubation at pH 3.5, wherein retaining essentially the same viability after the incubation comprises generating at least 50% of the number of CFU after the incubation as compared to the number of CFU generated before the incubation.

9. The method of claim 2, wherein at least one bacterial strain comprised in the composition retains essentially the same viability after a 4 hour of incubation in the presence of a 0.45% bile extract, wherein retaining essentially the same viability after the incubation comprises generating at least 50% of the number of CFU after the incubation as compared to the number of CFU generated before the incubation.

10. The method of claim 2, wherein at least one bacterial strain comprised in the composition has all of the following antimicrobial activities, as evidenced by inhibition zones determined by the spot on lawn assay: (i) a 10 mm or greater inhibition zone for *Salmonella*, (ii) a 9 mm or greater inhibition zone for *Listeria monocytogenes*, (iii) a 9 mm or greater inhibition zone for *Staphyloccocus aureus*, (iv) a 10 mm or greater inhibition zone for *Escherichia coli*.

11. A method for treating or preventing diarrhea caused by a viral infection in a subject in need thereof, comprising administering to said subject a composition comprising a mixture of bacterial strains, wherein the bacterial strains belong to the bacterial species *Lactobacillus plantarum* and *Lactobacillus reuteri*, wherein the bacterial strains have at least one of the following antimicrobial activities, as evidenced by inhibition zones determined by the spot on lawn assay: (i) a 10 mm or greater inhibition zone for *Salmonella*, (ii) a 9 mm or greater inhibition zone for *Listeria monocytogenes*, (iii) a 9 mm or greater inhibition zone for *Staphyloccocus aureus*, (iv) a 10 mm or greater inhibition zone for *Escherichia coli*; and
  wherein the composition is administered as at least one dose within the first 48 hours after birth of the subject.

12. The method of claim 11, wherein the composition further comprises at least one bacterial strain belonging to the genera selected from the group consisting of *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus* and *Weisella*, wherein the composition does not comprise a *Lactobacillus fermentum* bacterial strain deposited at the Spanish Type Cultures Collection on May 16, 2013 under deposit number CECT 8347 (AqSynJ12) or a *Lactobacillus mucosae* bacterial strain deposited at the Spanish Type Cultures Collection on May 16, 2013 under deposit number CECT 8349 (AqSynJ55).

* * * * *

UNITED STATES PATENT AND TRADEMARK OFFICE
CERTIFICATE OF CORRECTION

PATENT NO. : 10,179,153 B2
APPLICATION NO. : 15/520622
DATED : January 15, 2019
INVENTOR(S) : Pedro Miguel Rubio Nistal et al.

It is certified that error appears in the above-identified patent and that said Letters Patent is hereby corrected as shown below:

In the Claims

At Column number 32, Line number 22, Claim 7 delete "strain at least one strain, and comprised in the composition" and replace it with -- strain comprised in the composition --

Signed and Sealed this
Ninth Day of April, 2019

Andrei Iancu
*Director of the United States Patent and Trademark Office*